(12) United States Patent
Hatton et al.

(10) Patent No.: US 10,286,355 B2
(45) Date of Patent: May 14, 2019

(54) SYSTEMS AND METHODS INCORPORATING IONIC LIQUIDS FOR ELECTROCHEMICALLY MEDIATED CAPTURING OF LEWIS ACID GASES

(71) Applicant: Massachusetts Institute of Technology, Cambridge, MA (US)

(72) Inventors: Trevor Alan Hatton, Sudbury, MA (US); Paul Brown, Cambridge, MA (US); Sahag Voskian, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 15/660,587

(22) Filed: Jul. 26, 2017

(65) Prior Publication Data

US 2018/0028962 A1 Feb. 1, 2018

Related U.S. Application Data

(60) Provisional application No. 62/367,206, filed on Jul. 27, 2016.

(51) Int. Cl.
| | |
|---|---|
| *B01D 53/32* | (2006.01) |
| *B01D 53/14* | (2006.01) |
| *B01D 53/62* | (2006.01) |
| *B01D 53/78* | (2006.01) |
| *B01D 53/94* | (2006.01) |
| *B01D 53/96* | (2006.01) |
| *C25B 9/06* | (2006.01) |
| *C07C 211/09* | (2006.01) |

(Continued)

(52) U.S. Cl.
CPC ....... *B01D 53/1475* (2013.01); *B01D 53/326* (2013.01); *B01D 53/62* (2013.01); *C01B 32/50* (2017.08); *C07C 211/09* (2013.01); *C25B 9/06* (2013.01); *B01D 53/1425* (2013.01); *B01D 2252/2041* (2013.01); *B01D 2252/30* (2013.01); *B01D 2257/504* (2013.01); *B01D 2258/0283* (2013.01); *B01D 2259/80* (2013.01); *C07C 211/10* (2013.01); *C07C 2531/30* (2013.01); *C07F 1/08* (2013.01); *Y02C 10/04* (2013.01); *Y02C 10/06* (2013.01); *Y02P 20/152* (2015.11); *Y02P 20/51* (2015.11)

(58) Field of Classification Search
None
See application file for complete search history.

(56) References Cited

U.S. PATENT DOCUMENTS

| | | |
|---|---|---|
| 2006/0081482 A1 | 4/2006 | Tempel et al. |
| 2007/0287812 A1 | 12/2007 | McDermott et al. |
| | (Continued) | |

OTHER PUBLICATIONS

International Search Report and Written Opinion dated Oct. 3, 2017 for Application No. PCT/US2017/043955.

(Continued)

*Primary Examiner* — Daniel Berns
(74) *Attorney, Agent, or Firm* — Wolf, Greenfield & Sacks, P.C.

(57) ABSTRACT

The present invention generally relates to methods and systems for capturing a Lewis acid gas (e.g., $CO_2$). In some embodiments, the methods and systems utilize an ionic liquid incorporated into one or more electrochemical cells.

20 Claims, 8 Drawing Sheets

(51) Int. Cl.
*C07C 211/10* (2006.01)
*C07F 1/08* (2006.01)
*C01B 32/50* (2017.01)

(56) References Cited

U.S. PATENT DOCUMENTS

2008/0083606 A1    4/2008    Volland et al.
2010/0242728 A1*   9/2010    Radosz .................. B01D 53/04
                                                                          95/106
2016/0114290 A1    4/2016    Stern et al.

OTHER PUBLICATIONS

Brown et al., Enhanced gravimetric $CO_2$ capacity and viscosity for ionic liquids with cyanopyrrolide anion. AIChE J. Jul. 2015;61(7):2280-5. Epub Apr. 13, 2015.

Brown et al., $CO_2$-responsive microemulsions based on reactive ionic liquids. Langmuir. Apr. 22, 2014;30(15):4267-72. doi: 10.1021/la500675g. Epub Apr. 1, 2014.

Deutsch et al., Retrofitting of coal-fired power plants for $CO_2$ emissions reductions. An MIT Energy Initiative Symposium. Massachusetts Institute of Technology. Mar. 23, 2009. 7 pages.

Fredlake et al., Thermophysical properties of imidazolium-based ionic liquids. J. Chem. Eng. Data. 2004;49:954-64, doi:10.1021/je034261a. Epub Jun. 10, 2004.

Gurkan et al., Equimolar $CO_2$ absorption by anion-functionalized ionic liquids. J Am Chem Soc. Feb. 2010;132(7):2116-7. doi: 10.1021/ja909305t. Epub Feb. 1, 2010.

Iida et al., Properties of ionic liquids containing silver(I) or protic alkylethylenediamine cations with a bis(trifluoromethanesulfonyl)amide anion. J Colloid Interface Sci. Apr. 15, 2011;356(2):6308. doi: 10.1016/jjcis.2011.01.070. Epub Jan. 27, 2011.

Lin et al., Metal-containing ionic liquids and ionic liquid crystals based on imidazolium moiety. J Organomet Chem. Aug. 1, 2005;690(15):3498-512. Epub Apr. 19, 2005.

Mehdi et al., Hydrophobic ionic liquids with strongly coordinating anions. Chem Commun (Camb). Jan. 14, 2010;46(2):234-6. doi: 10.1039/b914977e. Epub Nov. 21, 2009.

Prodius et al., Catalytic "triangles": binding of iron in task-specific ionic liquids. Chem Commun (Camb). Mar. 7, 2013;49(19):1915-7. doi: 10.1039/c2cc36741f. Epub Oct. 22, 2012.

Rochelle, Amine scrubbing for $CO_2$ capture. Science. Sep. 25, 2009;325(5948):1652-4. doi: 10.1126/science.1176731.

Schaltin et al., Room-temperature silver-containing liquid metal salts with nitrate anions. Phys Chem Chem Phys. Nov. 21, 2013;15(43):18934-43. doi: 10.1039/c3cp53263a. Epub Oct. 4, 2013.

Song et al., Aza-crown ether complex cation ionic liquids: preparation and applications in organic reactions. Chem Eur J. Sep. 26, 2014;20(40):12894-900. doi: 10.1002/chem.201403118. Epub Aug. 22, 2014.

Stern et al., An electrochemically mediated gas separation process for carbon abatement. Energy Proc. 2013;37:1172-9.

Stern et al., Bench-scale demonstration of $CO_2$ capture with electrochemically-mediated amine regeneration. RSC Advances. 2014;4:5906-5914. Epub Nov. 29, 2013.

Takemura et al., Solvation structure of a copper(II) ion in protic ionic liquids comprising N-hexylethylenediamine. Inorg Chem. Sep. 15, 2014;53(18):9667-78. doi: 10.1021/ic501177t. Epub Sep. 4, 2014.

Washiro et al., Highly ion conductive flexible films composed of network polymers based on polymerizable ionic liquids. Polymer. 2004;45(5): 1577-82.

Zhang et al., Ionic liquids with metal chelate anions. Chem Commun (Camb). Feb. 25, 2012;48(17):2334-6. doi: 10.1039/c2cc16906a. Epub Dec. 14, 2011.

Gutowski et al., Amine-functionalized task-specific ionic liquids: A mechanistic explanation for the dramatic increase in viscosity upon complexation with $CO_2$ from molecular simulation. J Am Chem Soc. 2008;130(44):14690-704. Epub Oct. 11, 2008.

* cited by examiner

SYSTEMS AND METHODS INCORPORATING IONIC LIQUIDS FOR ELECTROCHEMICALLY MEDIATED CAPTURING OF LEWIS ACID GASES

RELATED APPLICATIONS

This application claims the benefit of U.S. Provisional Patent Application Ser. No. 62/367,206, filed Jul. 27, 2016, herein incorporated by reference.

FIELD OF THE INVENTION

The present invention generally relates to methods and systems for capturing Lewis acid gases, such as $CO_2$. In some embodiments, the methods and systems utilize an ionic liquid incorporated into one or more electrochemical cells.

BACKGROUND OF THE INVENTION

There is often a need to remove Lewis acid gases from gas mixtures. For example, there is a long-term need to suppress $CO_2$ emissions from the burning of fossil fuels to avoid dangerous anthropogenic interference with the climate system. For example, in 2014, around 2.2 billion tons of $CO_2$ were generated from coal-fired electric power plants in the US, representing 40% of the nation's emissions. There is, therefore, a necessity to stem this release by developing post-combustion carbon capture technologies, which may be added to new plants or retrofitted to existing plants. One technology involves thermal amine scrubbing, which uses cold solutions of amines to bind to $CO_2$ and reverses this binding by elevating the temperature. This was recently implemented at the Boundary Dam power station in Canada, to capture up to 1 million tons of $CO_2$ per year. However, associated with this process is a large enthalpy of reaction and a significant energy cost to release the $CO_2$, as well as heat lost to water vaporization (~85 kJ $mol^{-1}$ at 40° C.). In addition, in many power plants (as well as non-power generating industrial processes) there is not always enough steam to operate a thermal swing system.

Accordingly, improved methods and systems are needed.

SUMMARY OF THE INVENTION

The present invention generally relates to methods and systems for capturing designated gases. In some embodiments, the gas may be a Lewis acid gas (e.g., $CO_2$, $SO_2$, boranes, etc.). According to one or more embodiments a system for capturing a Lewis acid gas (e.g., $CO_2$) is provided. The system may comprise a first zone comprising a functional ionic liquid comprising a cation and an anion; and a second zone in fluid connection with the first zone comprising a complexation agent capable of associating and/or disassociating the cation to and/or from the functional ionic liquid upon exposure to an electrical potential.

According to one or more embodiments, a method for capturing a Lewis acid gas (e.g., $CO_2$, $SO_2$, boranes, etc.) is provided. The method may comprise providing a system comprising a first zone and a second zone in fluid connection with the first zone. The first zone may comprise a functional ionic liquid comprising a cation and an anion. The second zone may comprise a complexation agent capable of associating and/or disassociating the cation to and/or from the functional ionic liquid upon exposure to an electrical potential. The method may further comprise exposing the ionic liquid to the Lewis acid gas in the first zone, wherein the cation associates with the Lewis acid gas to form a cation-Lewis-acid-gas complex; and exposing the cation-Lewis-acid-gas complex to the complexation agent in the second zone, wherein the complexation agent associates with the cation to forma a cation-complexation agent complex and the Lewis acid gas is released to form free Lewis acid gas.

Other aspects, embodiments, and features of the invention will become apparent from the following detailed description when considered in conjunction with the accompanying drawings. The accompanying figures are schematic and are not intended to be drawn to scale. For purposes of clarity, not every component is labeled in every figure, nor is every component of each embodiment of the invention shown where illustration is not necessary to allow those of ordinary skill in the art to understand the invention. All patent applications and patents incorporated herein by reference are incorporated by reference in their entirety. In case of conflict, the present specification, including definitions, will control.

DETAILED DESCRIPTION

The present invention generally relates to methods and systems for capturing a gas, such as Lewis acid gases, including $CO_2$. In some embodiments, the methods and systems described herein utilize a chemically reversible electrochemical reaction involving a complexation agent and an ionic liquid. In some cases, the complexation agent is capable of associating a cation from the ionic liquid upon exposure to an electrical potential. In some cases, the complexation agent is capable of dissociating a cation to the ionic liquid upon exposure to an electrical potential.

According to one or more embodiments, the electrochemically-mediated regeneration of ionic liquids described herein may be employed as a novel, cost-effective methods and systems to capture and/or remove a Lewis acid gas (e.g., $CO_2$, $SO_2$, boranes, etc.,) from a gas.

According to one or more embodiments, the electrochemically-mediated regeneration of ionic liquids described herein may be employed as a novel, cost-effective methods and systems to capture and/or remove $CO_2$ from a gas (e.g., a flue gas). According to one or more embodiments, gas desorption (e.g., $CO_2$ desorption) is achieved through the oxidation of a copper electrode releasing cupric ions into the ionic liquid electrolyte, which chelated to the ionic liquid cations and displaced Lewis acid gas (e.g., $CO_2$), rather than through utilizing an energy intensive thermal swing to drive gas desorption.

While the description herein often makes reference to $CO_2$ as the specific Lewis acid gas, a person of ordinary skill would understand that this description could generally be applied to other Lewis acid gases, including, without limitation, $SO_2$ and boranes.

Figure 1:
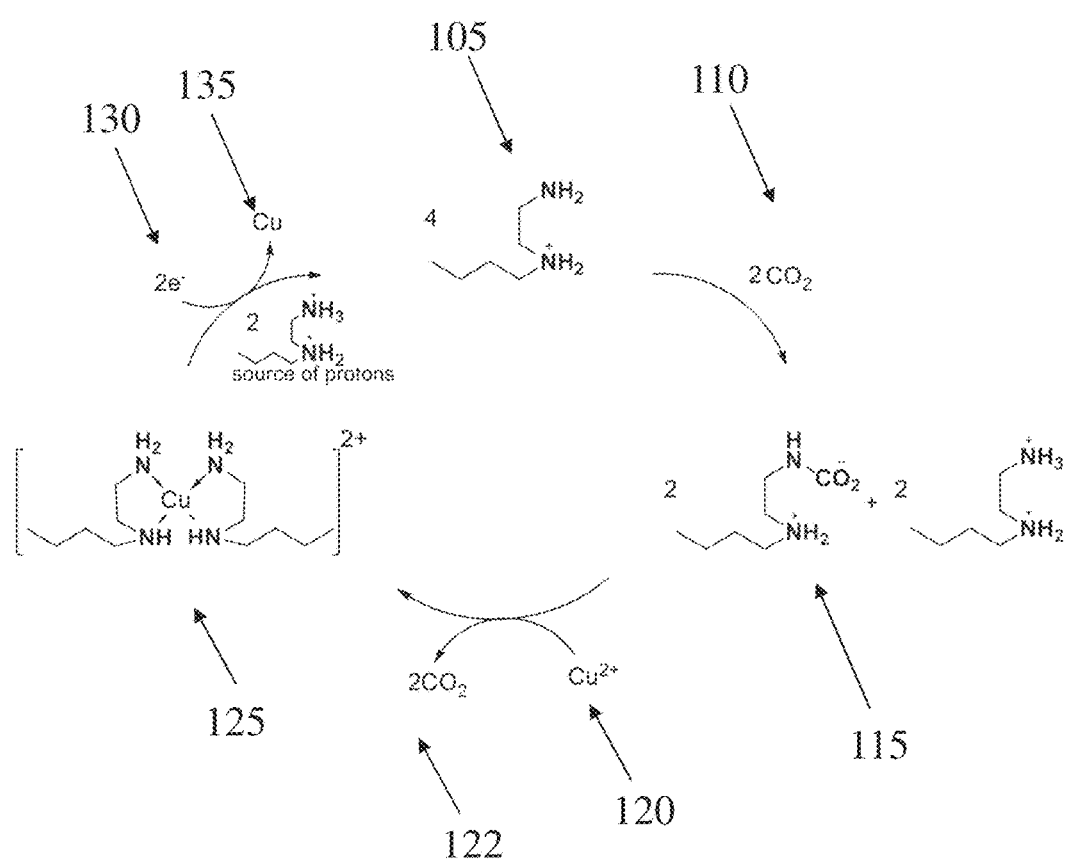
FIG. 1 represents a process flow diagram of a method for capturing $CO_2$, according to one or more embodiments.

A non-limiting example of a scheme for capturing $CO_2$ using a complexation agent and an ionic liquid is shown in FIG. 1. In this figure, the complexation agent is copper and the functional ionic liquid comprises the cation of N-butylethylenediaminium. The complexation agent and ionic liquid should be viewed as exemplary, and those of ordinary skill in the art will be able to apply the teachings of this scheme to other complexation agents and ionic liquids. Complexation agents and ionic liquids are described in more detail herein.

In FIG. 1, cation 105, N-butylethylenediaminium which comprises an ethylenediaminium group, of the functional ionic liquid is exposed to $CO_2$ 110 in a first zone, wherein the cation associates with the $CO_2$ to form cation-$CO_2$ complex 115. For example, the $CO_2$ may be scrubbed from a flue gas by the ionic liquid similar to those used in traditional thermal scrubbing systems, where the first zone comprises a flue gas scrubbing zone.

Next, cation-$CO_2$ complex 115 is exposed to complexation agent 120 (e.g., a copper-based complexation agent) in a second zone, wherein the complexation agent associates with the cation to form a cation-complexation agent complex 125 and $CO_2$ is released to as free $CO_2$ 122. For example, the ionic liquid saturated with cation-$CO_2$ complexes may be sent to an anode chamber of an electrochemical cell where a copper electrode is oxidized (corroded) to form cupric ions. These ions complex with the ionic liquid cation to form cation-complexation agent complex 125 and displace the $CO_2$ from the amine binding sites, thereby forming free $CO_2$ 122. The gas/liquid mixture may then be separated into a pure $CO_2$ stream and the copper-saturated sorbent stream (i.e., the component comprising the cation-copper complexes).

Next, cation-complexation agent complex 125 may be exposed to electrical current 130, thereby reforming complexation agent 135 (e.g., copper) and cation 105 upon exposure to protons. For example, the copper-saturated sorbent stream is directed to the cathode, where the cupric ions are exposed to electrical current (e.g., electrons 130) electroplated onto a separate copper electrode, which regenerates the sorbent stream's $CO_2$ absorbing capacity.

Without wishing to be bound by theory, ionic liquids disclosed herein can bind to $CO_2$, or other Lewis acid gases, with the additional advantage that a thermal swing is not necessarily required for desorption. Instead, desorption may be achieved by complexation to Cu(II). By utilizing this process instead of aqueous amine solutions, many challenges including solvent evaporation and the need for a supporting electrolyte are eliminated. In addition, the use of an ionic liquid lowers the overpotential required to reduce the Cu(II) but, if needed, may be increased, due to the large electrochemical windows, to drive the reaction.

The term Lewis acid gas is given its ordinary meaning in the art and generally refers to a gas that is a chemical species that contains an empty orbital which is capable of accepting an electron pair. Notable examples of Lewis acid gases include, without limitation: $CO_2$, $SO_2$, and boranes.

The term ionic liquid is given its ordinary meaning in the art and generally refers to salts that are in the liquid state below a select temperature, for example, 100° C. Generally, an ionic liquid comprises a cation and an anion. Ionic liquids may be used for thermal scrubbing applications due to their low volatility, high thermal stability, reduced potential for corrosion, and enhanced Lewis acid gas capacity. Ionic salts have negligible vapor pressure, good thermal stability and solvation for a wide variety of gases. In particular relevance to an electrochemically mediated system, the electrochemical windows of ionic liquids are exceptionally wide up to 6 V) as compared with water, which has an electrochemical window of 1 V). According to one or more embodiments, functional ionic liquids incorporated into the systems and methods disclosed herein may have chemical behavior that is analogous to amine solutions, but provide the advantages of serving as the sorbent, solvent, and the supporting electrolyte.

Without wishing to be bound by theory, while transition-metal salts are conventionally not very soluble in ionic liquids, it has been found that good dissolution can be achieved by complexing them with an ionic liquid. With this in mind, the electrochemistry presented herein is of significant interest as it involves the rare occurrence of electrodeposition from an ionic liquid with a metal-containing cation. The above is beneficial to metal deposition because the electroactive species can easily access the electrode surface compared to the more common anionic metal complexes, which must travel against the electric field and compete with other cations under reductive conditions, thus improving energy efficiency of the process. Such chelate-based ionic liquids offer many advantages of being able to act as recyclable catalysts for chemical transformations.

According to one or more embodiments a functional ionic liquid is provided comprising a cation that both facilitates Lewis acid gas (e.g., $CO_2$) capture and is capable of chelating to metal ions (e.g., cupric ions).

In some embodiments, the cation of the functional ionic liquid comprises a species represented by the structure shown in structural formula (I):

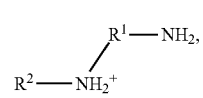

wherein:

$R^1$ has the formula: $(C(R)_2)_n$, in which R is selected from the group consisting of H or optionally substituted $C_1$-$C_3$ alkyl; and n is 1, 2, 3, 4, 5, or 6; and $R^2$ has the formula: $(C(R')_2)_m$—R", in which R' is selected from the group consisting of H or optionally substituted $C_1$-$C_3$ alkyl; R" is H or optionally substituted $C_1$-$C_3$ alkyl; and m is 1, 2, 3, 4, 5, 6, 7, 8, 9, or 10.

In some embodiments, R is selected from the group consisting of H or unsubstituted $C_1$-$C_3$ alkyl. In some embodiments, R' is selected from the group consisting of H or unsubstituted $C_1$-$C_3$ alkyl. In some embodiments, R" is selected from the group consisting of H or unsubstituted $C_1$-$C_3$ alkyl. In some embodiments, R" is unsubstituted $C_1$-$C_{10}$ alkyl. In some embodiments, R" is optionally substituted $C_1$-$C_5$ alkyl. In some embodiments, R" is unsubstituted $C_1$-$C_5$ alkyl. In some embodiments, R" is methyl, ethyl, n-propyl, i-propyl, n-butyl, i-butyl, or t-butyl. In some embodiments, R" is n-propyl. In some embodiments R" is a carbocyclealkyl group (cyclic hydrocarbon containing one or more double bonds), and cyclic hydrocarbon (heteroaryl).

Heteroaryl groups include, for example, pyrrole, furan, thiophene, imidazole, oxazole, thiazole, pyrazole, pyridine, pyrazine, pyridazine, and pyrimidine, and the like. In some embodiments R" is a vinyl group.

In some embodiments, the cation comprises an ethylenediaminium unit. In some embodiments, the ethylenediaminium unit may be represented by the structure shown in structural formula (II):

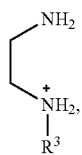
(II)

wherein $R^3$ is any suitable group.

In some embodiments, $R^3$ is selected from the group consisting of H, optionally substituted $C_1$ to $C_{10}$ alkyl, optionally substituted $C_6$ to $C_{10}$ cycloalkyl, optionally substituted $C_6$ to $C_{12}$ aryl, optionally substituted alkenyl (e.g., vinyl groups such as —CHCHR''', wherein R''' is a suitable group, for example optionally substituted alkyl or optionally substituted aryl, including phenyl), and optionally substituted $C_7$ to $C_{12}$ alkyl. In some embodiments, $R^3$ is optionally substituted $C_1$-$C_{10}$ alkyl. In some embodiments, $R^3$ is unsubstituted $C_1$-$C_{10}$ alkyl. In some embodiments, $R^3$ is optionally substituted $C_1$-$C_5$ alkyl. In some embodiments, $R^3$ is unsubstituted $C_1$-$C_5$ alkyl. In some embodiments, $R^3$ is methyl, ethyl, n-propyl, i-propyl, n-butyl, i-butyl, or t-butyl. In some embodiments, $R^3$ is n-propyl. In some embodiments $R^3$ is a carbocyclealkyl group (cyclic hydrocarbon containing one or more double bonds), and cyclic hydrocarbon (heteroaryl). Heteroaryl groups include, for example, pyrrole, furan, thiophene, imidazole, oxazole, thiazole, pyrazole, pyridine, pyrazine, pyridazine, and pyrimidine, and the like. In some embodiments $R^3$ is a vinyl group.

Non-limiting examples of any of the above-referenced optional substituents include OH, SH, $SR^i$, $SiH_3$, Cl, Br, F, I, $NH_2$, CN, $NO_2$, $COOR^i$, CHO, COC (ether), $COR^i$ and $OR^i$, wherein $R^i$ is a $C_1$ to $C_{10}$ alkyl or cycloalkyl group. In embodiments where more than one substituent is present, the substituents may be the same or different.

In some embodiments the cation may be dicationic or polycationic. For example, (4-Vinyl)benzoylethylene-diamine (VBEDA) may react with the appropriate acid to form an ionic liquid. The resulting monomer may be (co-)polymerized allowing for spin-coated or grafted layers, or the generation of sponges and thermoresponsive gels. Other polycations (which act as ionic liquid co-polymers) include polyimidazolium, polypyrrolidinium, polyallydimethylammonium, poly(3-acrylamidopropyl)trimethylammonium, amongst others. In the case of polymeric ionic liquids anions may be combinations.

In some embodiments, the ionic liquid (IL) (e.g., ethylenediamine functionalized ionic liquid) may demonstrate good Lewis acid gas (e.g., $CO_2$) absorption. According to some embodiments, ethylenediamine functionalized ionic liquid absorbs about 39 mg $CO_2$ per g IL at 35° C. According to one or more embodiments the electrolyte (which comprises the ionic liquid) is regenerated by electrodeposition of cupric ions at the cathode.

Non-limiting examples of anions of the functional ionic liquid further include, without limitation: halide, sulfate, sulfonate, carbonate, bicarbonate, phosphate, nitrate, nitrate, acetate, triflate, nonaflate, bis(triflyl)amide, trifluoroacetate, heptaflurorobutanoate, haloaluminate, triazolide, amino acid derivatives (e.g. proline with the proton on the nitrogen removed), tetrafluoride, phosphorus tetrafluoride, phosphorus hexafluoride, alkylsulfonate, fluoroalkylsulfonate, arylsulfonate, bis(alkylsulfonyl)amide, bis(fluoroalkylsulfonyl) amide, bis(arylsulfonyl)amide, (fluoroalkylsulfonyl) (fluoroalkylcarbonyl)amide, hydrogensulfate, alkyl sulfate, aryl sulfate, carboxylate, hydrogen phosphate, dihydrogen phosphate, hypochlorite, or an anionic site of a cation-exchange resin. In some embodiments, the anion is boron tetrafluoride, phosphorus hexafluoride, methanesulfonate, trifluoromethanesulfonate, benzenesulfonate, p-toluenesulfonate, bis(methanesulfonyl)amide, bis(trifluoromethanesulfonyl)amide, bis(benzenesulfonyl)amide, or bis(p-toluenesulfonyl)amide. In some embodiments, the anion is methanesulfonate, trifluoromethanesulfonate, benzenesulfonate, p-toluenesulfonate, bis(methanesulfonyl)amide, bis (trifluoromethanesulfonyl)amide, bis(benzenesulfonyl) amide, or bis(p-toluenesulfonyl)amide. In some embodiments, the anion is bis(methanesulfonyl)amide, bis (trifluoromethanesulfonyl)amide, bis(benzenesulfonyl) amide, or bis(p-toluenesulfonyl)amide. In some embodiments, the anion is bis(trifluoromethanesulfonyl)amide or (trifluoromethanesulfonyl)(trifluoroacetyl)amide. In some embodiments, the anion is bis(trifluoroethanesulfonyl)amide.

In some embodiments these anions may be dianionic or polyanionic. Examples of possible polyanions include polyvinyl sulfonates, polyphosphates, polycarboxylates, poly (acrylamide)-2-methylpropane sulfonate, polyacrylic acid, as well as those having trifluoromethanesulfonamide anions in their backbone [Polymer, 2004, 45, 1577-1582].

According to one or more embodiments the ionic liquid (e.g., functional ionic liquid) comprises N-butylethylenediaminium ("[HButylen]") as the cation species and bis(trifluoromethanesulfonyl)amide ("[$Tf_2N$]") as the anion species, having the structure shown in structural formula (III):

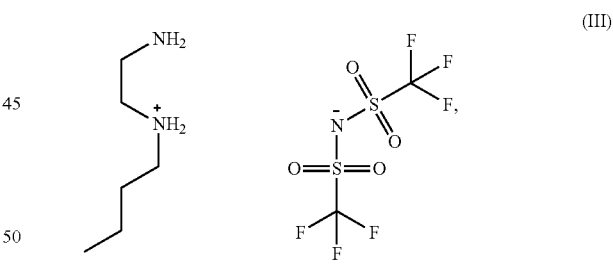
(III)

According to one or more embodiments, the system is also highly tunable allowing for improvements in physico-chemical properties such as viscosity and also in gravimetric $CO_2$, or other Lewis acid gas, capacity.

In some embodiments, a mixture comprising a functional ionic liquid and one or more diluent liquids may be employed. In some embodiments, the introduction of one or more diluent liquids may aid in reducing the viscosity, or altering the density, of the ionic liquid mixture (the resulting viscosity generally being a function of a linear mixing behavior of the constituents), thereby allowing the process to take place at a lower temperature, where the process may be optimized for efficiency. In some embodiments, the diluent liquid may be a diluent ionic liquid. In some embodiments the diluent liquid may comprise aqueous or non-aqueous solutions. In some embodiments the diluent liquid may comprise amines (e.g., monoethanol amine). In some embodiments the diluent liquid may comprise water, acetonitrile, ethanol, methanol, diethyl ether, chloroform, dimethylsulfoxide, methylpyrrolidone, dimethyl formamide, acetone, toluene, benzene, hexane, pentane, acetic acid, cyclopentane, dioxane, ethyl acetat, 2-ethylhexyal acetate, butyl acetate, benzyl benzoate, cottonseed oil, safflower oil, formic acid, acetic acid, etc., and any combinations thereof.

In some embodiments, a mixture comprising more than one ionic liquid may be employed. A first ionic liquid (also referred to as a primary or functional ionic liquid) may comprise the cations principally responsible for forming the cation-Lewis-acid-gas complexes to aid in capturing the Lewis acid gas (e.g., $CO_2$). One or more additional ionic liquids, also referred to as secondary ionic liquids or diluent ionic liquids, may be present in the system to modify physicochemical properties of the system, such as viscosity or density.

Non-limiting anions for a diluent ionic liquid include, without limitation: halide, sulfate, sulfonate, carbonate, bicarbonate, phosphate, nitrate, nitrate, acetate, $PF_6^-$, $BF_4^-$, triflate, nonaflate, bis(triflyl)amide, trifluoroacetate, heptaflurorobutanoate, haloaluminate, triazolide, and amino acid derivatives (e.g. proline with the proton on the nitrogen removed). Non-limiting examples of cations for a diluent ionic liquid include, without limitation: imidazolium, pyridinium, pyrrolidinium, phosphonium, ammonium, sulfonium, thiazolium, pyrazolium, piperidinium, triazolium, pyrazolium, oxazolium, guanidinium, 1-butyl-3-methylimidazolium ("[bmim]"), pyridazinium, pyrimidinium, pyrazinium, imidazolium, and dialkylmorpholinium. The diluent ionic liquid may comprise any combination of one or more anions and cations from the lists above. In some embodiments, the diluent ionic liquid is [bmim][BF] and/or [bmim][$PF_6$].

In some embodiments, the ionic liquid mixture may comprise the functional ionic liquid at between 20% to 100% by weight, between 20% to 80% by weight, between 30% to 70% by weight, between 30% to 60% by weight, or between 30% to 50% by weight, and the remainder being one or more diluent liquids.

In some embodiments, the introduction of one or more diluent liquids may aid in reducing the viscosity of the ionic liquid mixture (the resulting viscosity generally being a function of a linear mixing behavior of the constituents), thereby allowing the process to take place at a lower temperature, where the process may be optimized for efficiency. In some embodiments, the diluent liquid may be a diluent ionic liquid. In some embodiments the diluent liquid may comprise aqueous or non-aqueous solutions. In some embodiments the diluent liquid may comprise amines (e.g., monoethanol amine). In some embodiments the diluent liquid may comprise water, acetonitrile, ethanol, methanol, diethyl ether, chloroform, dimethylsulfoxide, methylpyrrolidone, dimethyl formamide, acetone, toluene, benzene, hexane, pentane, acetic acid, cyclopentane, dioxane, ethyl acetat, 2-ethylhexyal acetate, butyl acetate, benzyl benzoate, cottonseed oil, safflower oil, formic acid, acetic acid, etc., and any combinations thereof.

The methods and/or systems may be utilized at any suitable temperature. In some embodiments, the methods and/or systems are operated at about room temperature (e.g., about 25° C. In some embodiments, the methods and/or systems are operated at a temperature between about 25° C. and about 100° C., or between about 25° C. and about 90° C., or between about 25° C. and about 80° C., or between about 25° C. and about 75° C., between about 25° C. and about 70° C. A minimum temperature may be a temperature at which the ionic liquids remain liquids. According to some embodiments, the minimum temperature may be as low as −40° C., or in some cases even lower. A maximum temperature may be a temperature at which the components of the ionic liquid begin to breakdown, which takes place according to some embodiments at a temperature between about 250° C. and about 300° C.

A number of non-limiting examples of systems of the present disclosure will now be described in more detail. In some cases, a system comprises a first zone and a second zone. The first zone may comprise a functional ionic liquid comprising a cation and an anion. The term functional ionic liquid refers to an ionic liquid comprising an ion that binds with a species of interest (e.g., $CO_2$). Where the term "ionic liquid" appears herein, it may be understood that a functional ionic liquid is being referred to, unless the context in which the term appears suggests that a diluent ionic liquid is being described. The second zone may be in fluid connection with the first zone and comprise a complexation agent capable of associating and/or disassociating the cation to and/or from the functional ionic liquid upon exposure to an electrical potential. The first zone and the second zone may be in the same container/area or the two zones may be in different containers/areas which are in fluid connection with each other (e.g., such that there may be flow from the first zone to the second zone and vice versa). In some embodiments, the first zone comprises a first compartment or portion of an electrochemical cell and the second zone comprises a second compartment or portion of the electrochemical cell. In some embodiments, the first zone comprises a scrubber, and the second zone comprises a compartment or portion of the electrochemical cell.

The complexation agent may be contained in the ionic liquid, may be a portion of the electrode, and/or may be associated with an electrode.

In some embodiments, the first zone and the second zone may be the same. The term "fluid communication" as used herein refers to two components or regions containing a fluid, where the components or regions are connected together (e.g., by direct contact, or via a line, pipe, tubing, etc.) so that a fluid can flow between the two components or regions. Therefore, two chambers which are in "fluid communication" can, for example, be connected together by a line between the two chambers, such that a fluid or species present in the fluid can flow between the two chambers.

Figure 2:
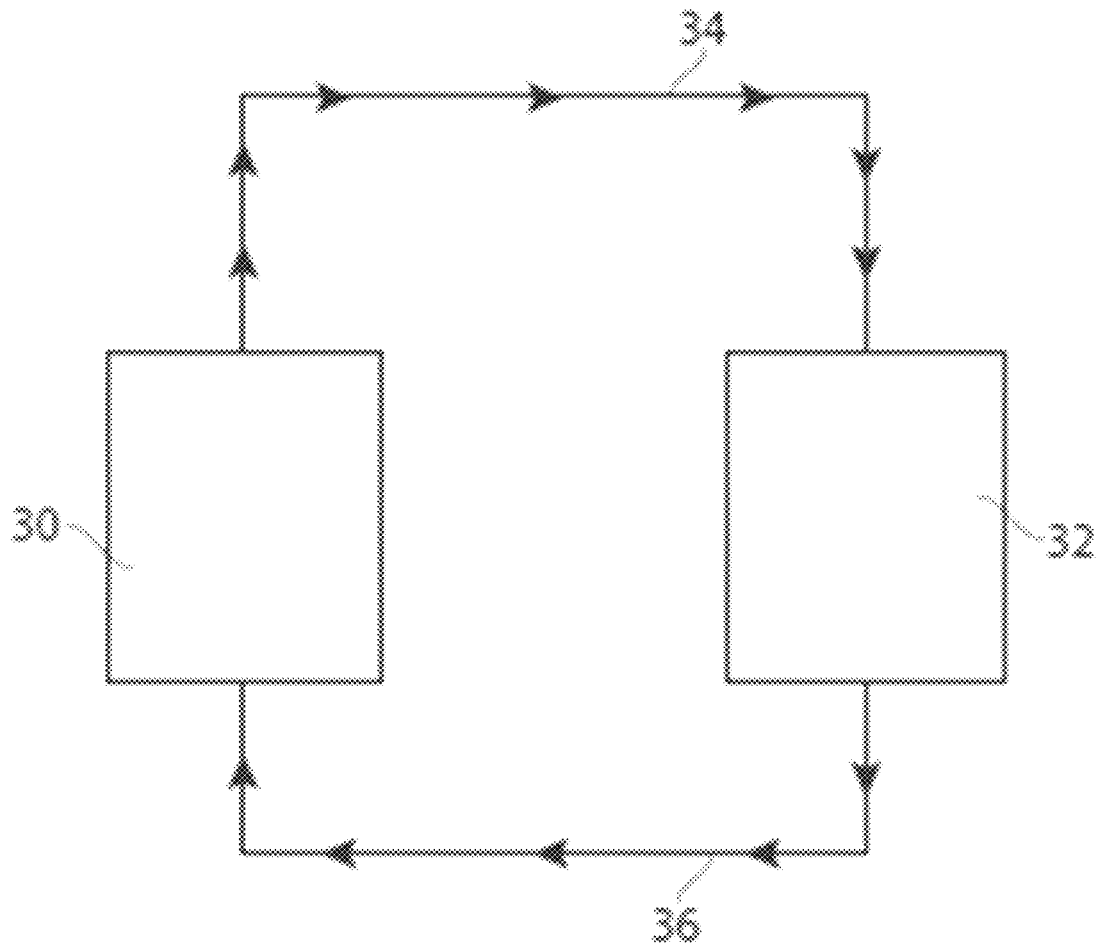
FIG. 2-FIG. 4 depict non-limiting systems of the present invention, according to some embodiments.

According to one or more embodiments, FIG. 2 shows the schematic of a system in which the steps described with regard to FIG. 1 may be performed. FIG. 2 shows a first zone 30 that comprises a functional ionic liquid comprising a cation and an anion. In the first zone exposing the ionic liquid to $CO_2$ in the first zone, wherein the cation associates with the $CO_2$ to form a cation-$CO_2$ complex. The complex may be directed to a second zone 32 through a conduit 34. The second zone 32 may comprise a complexation agent capable of associating and/or disassociating the cation to and/or from the functional ionic liquid upon exposure to an electrical potential. In the second zone 32, cation-$CO_2$ complex may be exposed to the complexation agent, wherein the complexation agent associates with the cation to form a cation-complexation agent complex and the $CO_2$ is released to form free $CO_2$. An additional regeneration step may take place to restore the cation, which may then be directed back to the first zone via conduit 36. Additional details made with regard to FIG. 1 may also apply to the system shown in FIG. 2 as would be understood by a person of ordinary skill in the art.

Figure 3:
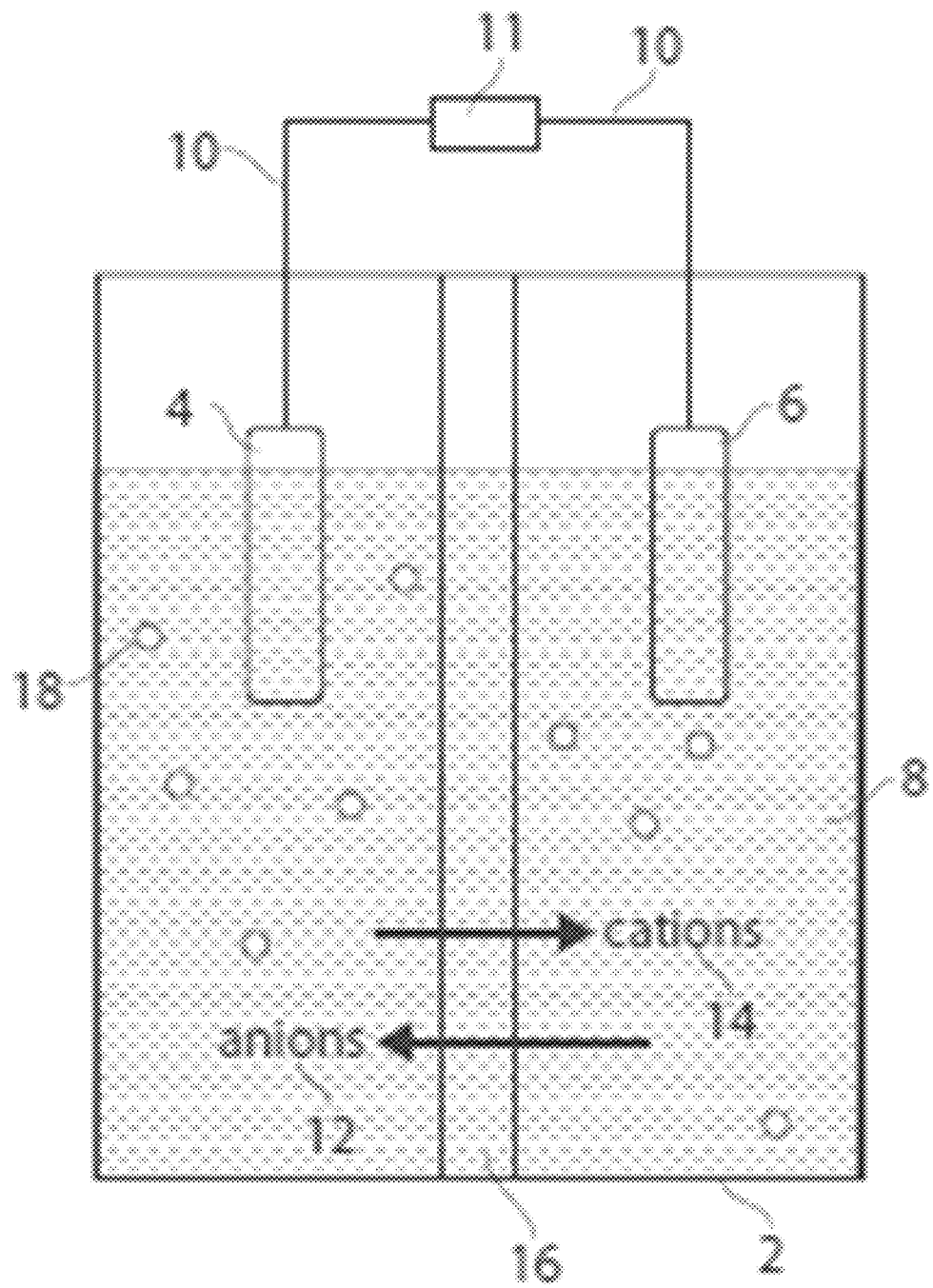

FIG. 3 shows a non-limiting example of a system of the invention or component thereof. For example, the electrochemical cell shown in FIG. 3. may form the second zone 32 as represented in FIG. 2 and described with regard to FIG. 1. In FIG. 3, the system comprises container 2, first electrode 4 (e.g., anode) in electrical communication with second electrode 6 (e.g., cathode) via circuit 10, and ionic liquid 8, functioning as an electrolytic solution, in contact with both first electrode 4 and second electrode 6. Circuit 10 may optionally comprise circuit component 11, e.g., power source, resistor, and/or capacitor. The system also comprises ion-permeable membrane 16 separating first electrode 4 from second electrode 6, and which allows for anions 12 to move from the first electrode side to the second electrode side and/or cations 14 to move from the second electrode side the first electrode side. Ion-migration balances the electroneutrality between the first electrode and the second electrode sides. The ionic liquid 8 contains complexation agent 18 (represented by circles).

Advantageously, the system may also be regenerated between batches by application of a second electrical potential, wherein application of a second electrical potential causes the complexation agent to return to its original form. It should also be understood that the system in FIG. 3 could readily be employed in embodiments where the complexation agent forms the electrode or a portion of the electrode (e.g., a solid complexation agent).

Figure 4:
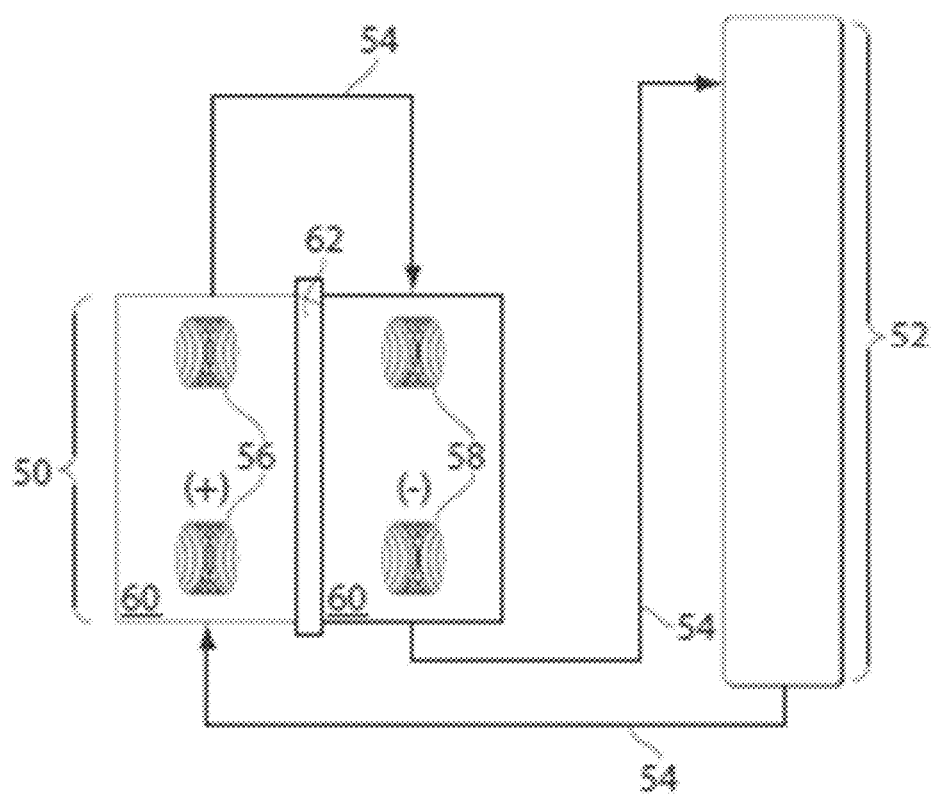

A specific example of a system as described in FIG. 2 is shown in FIG. 4. In FIG. 4, the system comprises a second zone 50 and a first zone 52 in fluid communication by fluid conduits 54. The second zone 50 comprises first electrode 56 (e.g., anode), second electrode 58 (e.g., cathode), ionic liquid 60, and membrane 62 (e.g., ion exchange membrane). In this figure, the complexation agent may be a portion of an electrode and/or may be contained in the ionic solution.

In a non-limiting example of a complexation agent for use in FIG. 3, the second electrode may comprise $Cu(OH)_2$ (e.g., such that the reaction at the second electrode is $Cu(OH)_2 + 2e^- \rightarrow Cu + 2OH^-$) and the first electrode may comprise Cu (e.g., such that the reaction at the first electrode is $Cu + 2OH^- \rightarrow Cu(OH)_2 + 2e^-$).

As used herein, a complexation agent generally refers to an agent (e.g., chemical entity) which is capable of associating with and/or dissociating from a cation upon exposure to an electrical potential. In some embodiments, the complexation agent is capable of associating with a cation upon exposure to a first electrical potential and is capable of dissociating the cation upon exposure to a second electrical potential which is more negative than the first electrical potential. Alternatively, in some embodiments, the complexation agent is capable of associating with a cation upon exposure to a first electrical potential and is capable of dissociating the cation upon exposure to a second electrical potential which is more positive than the first electrical potential. In some embodiments, the complexation agent is capable of associating a cation upon exposure to a first electrical potential and is capable of dissociating a cation upon exposure to a second electrical potential which is more negative than the first electrical potential. Generally, the complexation agent exhibits such reversible behavior upon exposure to different potentials. In some embodiments, the cation is a cation from an ionic liquid. As noted above, the complexation agent may be provided in an ionic liquid, may be a portion of the electrode, and/or may change phases depending on its environment. Generally, the complexation agent is a capable of associate and/or dissociating with a cation (e.g., from an ionic liquid) upon application of an electrical potential to the complexation agent.

Those of ordinary skill in the art will be aware that each type of complexation agent may require a different range of electrical potentials to cause association and/or dissociation of a cation.

In some cases, the association and/or dissociation of a cation requires an application of an electrical potential of about +/−0.1 volts, about +/−0.2 volts, about +/−0.3 volts, about +/−0.4 volts, about +/−0.5 volts, about +/−0.6 volts, about +/−0.7 volts, about +/−0.8 volts, about +/−0.9 volts, about +/−1 volts, about +/−1.1 volts, about +/−1.2 volts, about +/−1.3 volts, about +/−1.4 volts, about +/−1.5 volts, about +/−1.6 volts, about +/−1.7 volts about +/−1.8 volts, about +/−1.9 volts, about +/−2.0 volts, or about +/−2.5 volts. In some cases, the electrical potential is less than that required for the oxidation of water (e.g., −1.23 volts versus standard hydrogen electrode). In some embodiments, the application of the electrical potential is between about +/−0.1 and about +/−2.5 volts, or between about +/−0.1 and about +/−2 volts, or between about +/−0.1 and about +/−1.5 volts, or between about +/−0.1 and about +/−1 volts, or between about +/−0.5 and about +/−2.5 volts, or between about +/−0.5 and about +/−2 volts, or between about +/−1 and about +/−2.5 volts, or between about +/−1 and about +/−2 volts. Those of ordinary skill in the art will be aware of suitable methods and system for applying an electrical potential to a complexation agent (e.g., with use of a first electrode, a second electrode, and/or a power supply).

In some embodiments, the complexation agent is provided (e.g., as a solute) in an ionic liquid. The concentration of the complexation agent in the ionic liquid may be about 0.1 M, about 0.2 M, about 0.3 M, about 0.4 M, about 0.5 M, about 0.6 M, about 0.7 M, about 0.8 M, about 0.9 M, about 1 M, about 1.2 M, about 1.4 M, about 1.5 M, about 1.75 M, about 2 M, about 2.5 M, about 3 M, about 4 M, about 5 M, or greater. In some embodiments, the concentration of the complexation agent is between about 0.1 M and about 5 M, or between about 0.1 M and about 4 M, or between about 0.1 M and about 3 M, or between about 0.1 M and about 2 M, or between about 0.1 M and about 1 M, or between about 0.5 M and about 3 M, or between about 0.5 M and about 2 M.

In some embodiments, the complexation agent is provided as a solid. In some cases, the complexation agent may be formed on the surface of a substrate which is functioning as an electrode. In some cases, the electrode may comprise the complexation agent. In some cases, the electrode comprises the complexation agent, wherein at least about 10%, at least about 20%, at least about 30%, at least about 40%, at least about 50%, at least about 60%, at least about 70%, at least about 80%, at least about 90%, at least about 95%, at least about 98%, at least about 99%, or more, of the electrode by weight is the complexation agent.

The following equations describe non-limiting examples of complexation agents:

$$Cu + 2OH^- \Leftrightarrow CuO + H_2O + 2e^- \qquad (1)$$

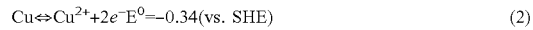

$$Cu \Leftrightarrow Cu^{2+} + 2e^- \quad E^0 = -0.34 (vs.\ SHE) \qquad (2)$$

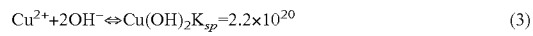

$$Cu^{2+} + 2OH^- \Leftrightarrow Cu(OH)_2 \quad K_{sp} = 2.2 \times 10^{20} \qquad (3)$$

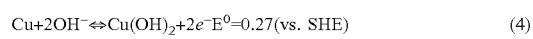

$$Cu + 2OH^- \Leftrightarrow Cu(OH)_2 + 2e^- \quad E^0 = 0.27 (vs.\ SHE) \qquad (4)$$

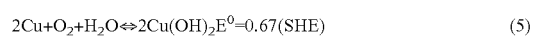

$$2Cu + O_2 + H_2O \Leftrightarrow 2Cu(OH)_2 \quad E^0 = 0.67 (SHE) \qquad (5)$$

In some embodiments, the complexation agent comprises Cu and/or CuO; Cu and/or Cu(OH)$_2$. In some embodiments, the complexation agent comprises nickel and/or nickel-based species. In some embodiments, the complexation agent comprising zinc and/or zinc-based species.

In some embodiments, the systems and/or methods may be used in applications involving gas scrubbing. Gas scrubbing is commonly employed to prevent the release of toxic chemicals (e.g., ammonia or hydrochloric acid) as well as greenhouse gases (e.g., carbon dioxide or sulfur dioxide) which are produced as byproduct in a variety of reactions.

In some embodiments, the systems and/or methods may be used in applications, wherein the reaction involves the capture and/or release of CO$_2$. Such systems provide many advantages over current methods, including lower costs, increased efficiency (e.g., due to the need for less heating), the ability to operate under higher pressures (if desired), and/or fewer side products. In addition, the system may be capable of being regenerated.

In some embodiments, a system/method for the capture of CO$_2$ from gaseous streams containing a mixture of gases is provided wherein at least a portion of the system/method comprises the conversion of CO$_2$ (e.g., to a dissolved species). Such systems may comprise the use of an amine (e.g., an ethylenediamine) in the functional ionic liquid. When the amine is present in the ionic liquid, the CO$_2$ and the amine can associate to form an amine-CO$_2$ complex. As a specific example of such a system, the process may comprise a complexation agents comprising copper. As will be known to those of ordinary skill in the art, Cu(II) is capable of coordinating with ligands containing amine groups. When removing Cu(II) from the solution, either Cu(I) species or Cu(0) could be formed to reduce the competition for CO$_2$.

Figure 5:
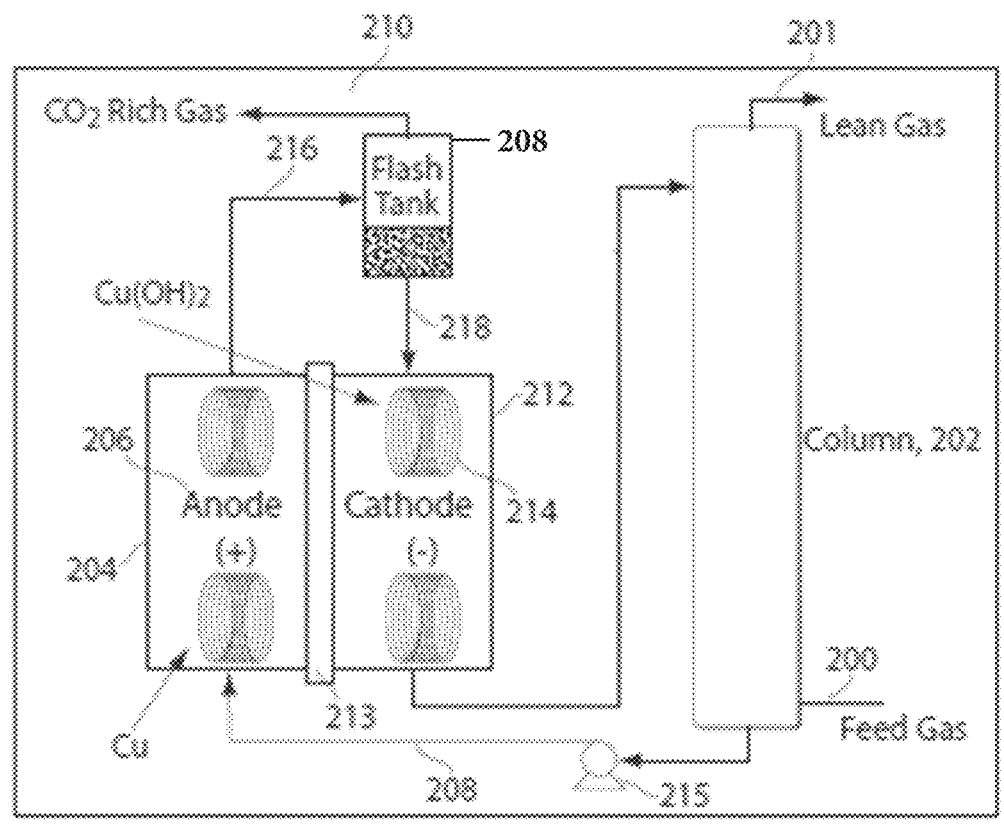
FIG. 5 depicts a non-limiting system of the present invention for use in the conversion of $CO_2$ to a dissolved species, according to some embodiments.

A non-limiting system can operate as follows and as illustrated in FIG. 5. A feed gas comprising CO$_2$ and other gaseous materials (e.g., N$_2$) is provided by inlet 200 and is flowed through column 202 which comprises an ionic liquid comprising primary functional amine cation species and out through outlet 201. During the flow through the column absorption of CO$_2$ via association with the amine cation to form an amine cation-CO$_2$ complex 6. The resulting complex is provided to anode container 204 containing anode 206. For example, the ionic liquid containing the complex may be flowed to anode container 204 via fluid connectors 208. The system may optionally comprise a pump (e.g., 215) which can be used to circulate the ionic liquid throughout the system. In this example, anode 206 comprises Cu(0). Upon application of an electrical potential to anode 206, Cu(II) ions may form. The Cu(II) ions may react with the CO$_2$-cation complex present in the ionic liquid, thereby causing CO$_2$ to be released and a copper-cation complex to form. This ionic liquid can be provided, optionally via flash tank 218 (e.g., to allow release and collection of CO$_2$ gas) to cathode container 212 comprising cathode 214. For example, the ionic liquid containing CO$_2$-cation complex may be flown via fluid conduit 216 to flash tank 208 wherein the CO$_2$ rich gas may be collected (e.g., via outlet 210), followed by flowing the ionic liquid via fluid conduit 218 to cathode container 212. Cathode container 214 and anode container 204 may be optionally separated by membrane 213. In cathode container 212, application of an electric potential can cause the copper-cation complex to dissociate, thereby reforming Cu(0) and regenerating the cation of the functional ionic liquid. Accordingly, FIG. 5 illustrates a regenerable system for the collection of CO$_2$ gas.

Those of ordinary skill in the art will be able to select other materials and reaction to which the above described systems/methods may be used.

In some embodiments, an electrode is utilized comprising a porous material, wherein the complexation agent intercalates into and/or de-intercalated from the electrode during operation of a system and/or a method. The term intercalate is given its ordinary meaning in the art and refers to the ability of an ion (e.g., a complexation agent such as copper) to insert into an electrode. An ion is said to reversibly intercalate if it can de-intercalate (e.g., deinsert), without unduly stressing the electrode, so that electrode performance is maintained over repeated cycling. For example, in some embodiments, the electrode comprises a porous material and the complexation agent (e.g., comprising copper) reversibly intercalates into the electrode by plating on the surface (e.g., include any pores, if present). In some embodiments, both the anode and the cathode are constructed such that complexation agent reversibly intercalates.

In some embodiments, use of a porous electrode as an intercalation/de-intercalation material for the complexation agent provides many advantages over use of a solid electrode with a solubilized complexation agent and/or an electrode formed of the complexation agent. For example, utilizing a intercalation/de-intercalation material may significantly improve the cycling stability of a system and/or a method, as the porous structure improves order and/or reversibility of the system and/or method as compared to use of a solid electrode formed of the complexation material and/or an electrode formed of material other than the complexation agent, wherein the complexation agent associates and/or dissociates from the outer surface of the electrode (e.g., a non-porous electrode).

The porous electrode may be made of any suitable material and/or may comprise any suitable shape or size. In a non-limiting embodiment, the electrode comprises a porous carbonaceous material. The term carbonaceous material is given its ordinary meaning in the art and refers to a material comprising carbon or graphite that is electrically conductive. Non-limiting example of carbonaceous materials include carbon nanotubes, carbon fibers (e.g., carbon nanofibers), and/or graphite. It should be understood that an electrode that comprises a carbonaceous material may be an electrode which consists or consists essentially of the carbonaceous material, or may be an electrode in which only a portion of the electrode comprises a carbonaceous material. For example, at least a portion of the electrode in electrical contact with the electrolyte may comprise a carbonaceous material. In such embodiments, the electrode may be partially fabricated from the carbonaceous material or the carbonaceous material may be deposited over an underlying material. The underlying material generally comprises a conductive material, for example, a metal. Other non-limiting examples of conductive materials are described herein.

In some embodiments, an electrode is porous. The porosity of an electrode may be measured as a percentage or fraction of the void spaces in the photoactive electrode. The percent porosity of an electrode may be measured using techniques known to those of ordinary skill in the art, for example, using volume/density methods, water saturation methods, water evaporation methods, mercury intrusion porosimetry methods, and nitrogen gas adsorption methods. In some embodiments, the electrode may be at least about 10% porous, at least about 20% porous, at least about 30% porous, at least about 40% porous, at least about 50% porous, at least about 60% porous, or greater. The pores may be open pores (e.g., have at least one part of the pore open to an outer surface of the electrode and/or another pore) and/or closed pores (e.g., the pore does not comprise an opening to an outer surface of the electrode or another pore). In some cases, the pores of an electrode may consist essentially of open pores (e.g., the pores of the electrode are greater than at least 70%, greater than at least 80%, greater than at least 90%, greater than at least 95%, or greater, of the pores are open pores). In some cases, only a portion of the electrode may be substantially porous. For example, in some cases, only a single surface of the electrode may be substantially porous. As another example, in some cases, the outer surface of the electrode may be substantially porous and the inner core of the electrode may be substantially non-porous. In a particular embodiment, the entire electrode is substantially porous.

In some embodiments, the ionic liquid functions as an electrolyte. An electrolyte, as known to those of ordinary skill in the art, is any substance containing free ions that is capable of functioning as an ionically conductive medium.

Various components of a system, such as the electrode, power source, electrolyte, separator, container, circuitry, insulating material, gate electrode, etc. can be fabricated by those of ordinary skill in the art from any of a variety of components, as well as those described in any of these patent applications described herein. Components may be molded, machined, extruded, pressed, isopressed, infiltrated, coated, in green or fired states, or formed by any other suitable technique. Those of ordinary skill in the art are readily aware of techniques for forming components of system herein.

In some embodiments, a system comprises at least one electrode, or at least two electrode, or two electrodes. In some cases, an electrode comprises a complexation agent, as described herein. In embodiments, wherein the electrode is not formed of the complexation agent, an electrode may comprise any material that is substantially electrically conductive. The electrode may be transparent, semi-transparent, semi-opaque, and/or opaque. The electrode may be a solid, semi-porous or porous. Non-limiting examples of electrodes include indium tin oxide (ITO), fluorine tin oxide (FTO), glassy carbon, metals, lithium-containing compounds, metal oxides (e.g., platinum oxide, nickel oxide), graphite, nickel mesh, carbon mesh, and the like. Non-limiting examples of suitable metals include gold, copper, silver, platinum, nickel, cadmium, tin, and the like. In some instances, the electrode may comprise nickel (e.g., nickel foam or nickel mesh). The electrodes may also be any other metals and/or non-metals known to those of ordinary skill in the art as conductive (e.g., ceramics). The electrode may be of any size or shape. Non-limiting examples of shapes include sheets, cubes, cylinders, hollow tubes, spheres, and the like. The electrode may be of any size. Additionally, the electrode may comprise a means to connect the electrode to another electrode, a power source, and/or another electrical device.

Various electrical components of system may be in electrical communication with at least one other electrical component by a means for connecting. A means for connecting may be any material that allows the flow of electricity to occur between a first component and a second component. A non-limiting example of a means for connecting two electrical components is a wire comprising a conductive material (e.g., copper, silver, etc.). In some cases, the system may also comprise electrical connectors between two or more components (e.g., a wire and an electrode). In some cases, a wire, electrical connector, or other means for connecting may be selected such that the resistance of the material is low. In some cases, the resistances may be substantially less than the resistance of the electrodes, electrolyte, and/or other components of the system.

In some embodiments, a power source may supply DC voltage to a system. Non-limiting examples include batteries, power grids, regenerative power supplies (e.g., wind power generators, photovoltaic cells, tidal energy generators), generators, and the like. The power source may comprise one or more such power supplies (e.g., batteries and a photovoltaic cell). In a particular embodiment, the power supply is a photovoltaic cell.

In some embodiments, a system may comprise a separating membrane (e.g., within an electrochemical cell). A separating membrane may be made of suitable material, for example, a plastic film. Non-limiting examples of plastic films included include polyamide, polyolefin resins, polyester resins, polyurethane resin, or acrylic resin and containing lithium carbonate, or potassium hydroxide, or sodium-potassium peroxide dispersed therein. In some cases, the membrane may be an anion exchange membrane and/or cation exchange membrane (i.e., ones with anion and/or cation exchangeable ions) which are readily available from commercial sources. Non-limiting examples of anionic exchange membranes include poly(ethylene-co-tetrafluoroethylene), poly(hexafluoropropylene-co-tetrafluoroethylene), poly(epichlorhydrin-ally glycidyl ether), poly(ether imide), poly(ethersulfone) cardo, poly(2,6-dimethyl-1,4-phenylene oxide), polysulfone, or polyethersulfone, associated with a plurality of cationic species (e.g., quaternary ammonium groups, phosphonium groups, etc.).

A container may be any receptacle, such as a carton, can, or jar, in which components of a system may be held or carried. A container may be fabricated using any known techniques or materials, as will be known to those of ordinary skill in the art. For example, in some instances, the container may be fabricated from gas, polymer, metal, and the like. The container may have any shape or size, providing it can contain the components of the system. Components of the system may be mounted in the container. That is, a component (e.g., an electrode) may be associated with the container such that it is immobilized with respect to the container, and in some cases, is supported by the container. A component may be mounted to the container using any common method and/or material known to those skilled in the art (e.g., screws, wires, adhesive, etc.). The component may or might not physically contact the container. In some cases, an electrode may be mounted in the container such that the electrode is not in contact with the container, but is mounted in the container such that it is suspended in the container.

Reagents may be supplied to and/or removed from a system using a commonly known transport device. The nature of the reagent delivery may vary with the type of fuel and/or the type of device. For example, solid, liquid, and gaseous reagents may all be introduced in different manners. The reagent transport device may be a gas or liquid conduit such as a pipe or hose which delivers or removes fuel, such as hydrogen gas or methane, from the system and/or from the reagent storage device. Alternatively, the system may comprise a movable gas or liquid storage container, such as a gas or liquid tank, which may optionally be physically removed from the system after the container is filled with reagent.

As used herein, the term "alkyl" is given its ordinary meaning in the art and may include saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer. Likewise, cycloalkyls have from about 3 to about 10 carbon atoms in their ring structure, and alternatively about 5, 6 or 7 carbons in the ring structure.

The term "heteroalkyl" is given its ordinary meaning in the art and refers to alkyl groups as described herein in which one or more atoms is a heteroatom (e.g., oxygen, nitrogen, sulfur, and the like).

The term "alkenyl" is given its ordinary meaning in the art and refers to unsaturated aliphatic groups analogous in length and possible substitution to the alkyls described above, but that contain at least one double or triple bond, respectively. In certain embodiments, the alkyl and alkenyl groups employed in the invention contain 1-20 aliphatic carbon atoms. In certain other embodiments, the alkyl and alkenyl groups employed in the invention contain 1-10 aliphatic carbon atoms.

The term "aryl" is given its ordinary meaning in the art and refers to single-ring aromatic groups such as, for example, 5-, 6- and 7-membered single-ring aromatic groups. The term "heteroaryl" is given its ordinary meaning in the art and refers to aryl groups as described herein in which one or more atoms is a heteroatom (e.g., oxygen, nitrogen, sulfur, and the like). Examples of aryl and heteroaryl groups include, but are not limited to, phenyl, pyrrolyl, furanyl, thiophenyl, imidazolyl, oxazolyl, thiazolyl, triazolyl, pyrazolyl, pyridinyl, pyrazinyl, pyridazinyl and pyrimidinyl, and the like. It should be understood that, when aryl and heteroaryl groups are used as ligands coordinating a metal center, the aryl and heteroaryl groups may have sufficient ionic character to coordinate the metal center. For example, when a heteroaryl group such as pyrrole is used as a nitrogen-containing ligand, as described herein, it should be understood that the pyrrole group has sufficient ionic character (e.g., is sufficiently deprotonated to define a pyrrolyl) to coordinate the metal center. In some cases, the aryl or heteroaryl group may comprise at least on functional group that has sufficient ionic character to coordinate the metal center, such as a biphenolate group, for example.

As used herein, the term "substituted" is contemplated to include all permissible substituents of organic compounds, "permissible" being in the context of the chemical rules of valence known to those of ordinary skill in the art. In some cases, "substituted" may generally refer to replacement of a hydrogen with a substituent as described herein. However, "substituted," as used herein, does not encompass replacement and/or alteration of a key functional group by which a molecule is identified, e.g., such that the "substituted" functional group becomes, through substitution, a different functional group. For example, a "substituted phenyl" group must still comprise the phenyl moiety and cannot be modified by substitution, in this definition, to become, e.g., a cyclohexyl group. In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

Examples of substituents include, but are not limited to, lower alkyl, lower aryl, lower aralkyl, lower cyclic alkyl, lower heterocycloalkyl, hydroxy, lower alkoxy, lower aryloxy, perhaloalkoxy, aralkoxy, lower heteroaryl, lower heteroaryloxy, lower heteroarylalkyl, lower heteroaralkoxy, azido, amino, halogen, lower alkylthio, oxo, lower acylalkyl, lower carboxy esters, carboxyl, -carboxamido, nitro, lower acyloxy, lower aminoalkyl, lower alkylaminoaryl, lower alkylaryl, lower alkylaminoalkyl, lower alkoxyaryl, lower arylamino, lower aralkylamino, lower alkylsulfonyl, lower-carboxamidoalkylaryl, lower-carboxamidoaryl, lower hydroxyalkyl, lower haloalkyl, lower alkylaminoalkylcarboxy-, lower aminocarboxamidoalkyl-, cyano, lower alkoxyalkyl, lower perhaloalkyl, lower arylalkyloxyalkyl, and the like.

The following examples are intended to illustrate certain embodiments of the present invention, but do not exemplify the full scope of the invention.

Example 1

In a non-limiting example, ionic liquids were synthesized and tested.

[HButylen][Tf$_2$N] was synthesized via acid-base neutralization of starting materials. Fundamental physicochemical properties were first investigated as they are essential when considering scale-up and application. Differential scanning calorimetry provided evidence of a melting point around 33° C. (which could be tuned by control of the cation architecture). Through thermogravimetric analysis (TGA) $T_{onset}$ was determined to be 329° C. The high thermal stability is typical of ionic liquids containing the [Tf$_2$N] anion. Finally, the density, p, was measured as a function of temperature. At 40° C. the density was measured to be 1.355 g cm$^{-3}$ and the ionic liquid had a thermal expansion coefficient, $\alpha_p$=7.66× 10-4° C.$^{-1}$. Importantly, for considering any application this value is relatively small.

N-hexylethylenediaminium bis(trifluoroethanesulfonyl) amide was synthesized and tested. It was found to have a melting point below −40° C., and a density of 1.31 g cm$^{-3}$ at 40° C. Because of the low melting point, this ionic liquid may be utilized at room temperature, if so desired.

Example 2

Figure 6:
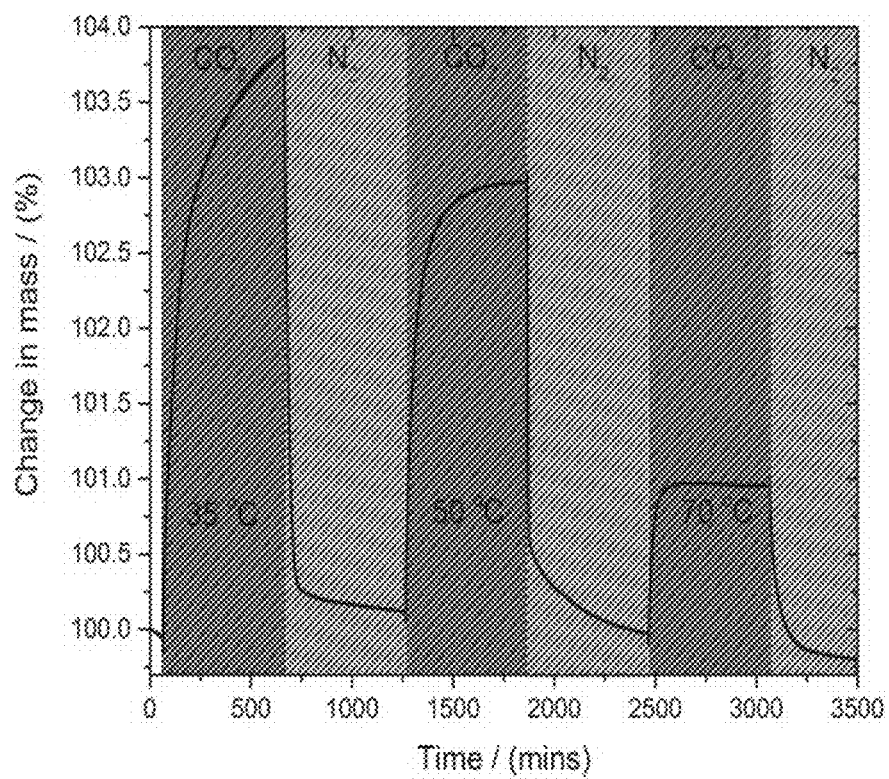
FIG. 6 shows a plot of absorption and desorption of $CO_2$ in [HButylen][$Tf_2N$] at 35° C., 50° C., and 70° C.

In a non-limiting example, the reaction of the ionic liquid, [HButylen][Tf$_2$N], (described in Example 1) was demonstrated by thermogravimetric analysis, as shown in the graph in FIG. 6. Generally, two moles of ionic liquid bind with 1 mole of $CO_2$. Complete chemical absorption would lead to a gravimetric capacity of 55.4 mg of $CO_2$ per g IL. In addition, heavy fluorinated anion also allows for enhanced physical absorption due to weak halogen bonds with $CO_2$. At 35° C. a 3.5% increase in mass is observed (though after 600 minutes a plateau was not yet reached), equating to 0.703 moles of $CO_2$ per two moles of IL. This is lower than a predicted 2:1 molar absorbance reflecting the finite temperature-dependent reversibility of the reaction, and is highlighted at higher temperatures. However, it is clear that this capacity was obtained rapidly.

Example 3

Figure 7:
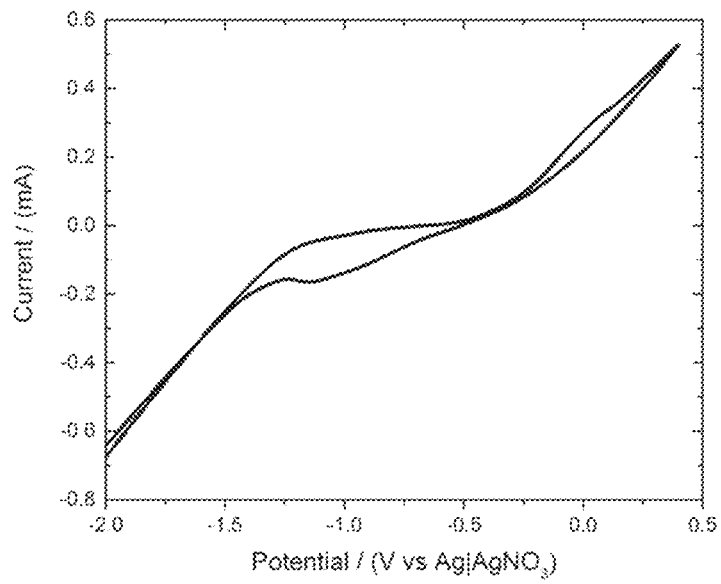
FIG. 7 shows a plot of a cyclic voltammogram of [HButylen][$Tf_2N$] at 50° C. under $N_2$ at 10 mV/s with Cu working electrode, Pt counter electrode and AglAgNO$_3$ reference electrode.

The cyclic voltammogram of [HButylen][Tf$_2$N] at 50° C. (due to m.p. and viscosity considerations) in FIG. 7 shows two redox couples, one at 0.02 V corresponding to the Cu(II)|Cu(I) and another at −1.01 V corresponding to Cu(I)|Cu(0). The copper working electrode is corroded (oxidized) to Cu(I) which is released to the diffusion layer of the electrode and is then oxidized to Cu(II) which is chelated by the cation of the ionic liquid [23]. The copper in this complex is later reduced to Cu(I), which results in the dissociation of [Cu(Butylen)$_2$][Tf$_2$N]$_2$ complex and subsequently Cu(I) is reduced to Cu(0) and is deposited onto the copper working electrode or precipitates as fine copper particles. Therefore, an electrochemical window wider than ~1V is sufficient to effect the corrosion of the copper electrode to Cu(II), however, a larger potential difference was used in the release experiment to achieve higher rates of release due to the larger overpotential.

Example 4

In a non-limiting example, TGA results indicate that saturation of [HButylen][Tf$_2$N] with $CO_2$ at temperature between 50° C. and 70° C. is achieved within 30 minutes. After two hours of purging in an electrochemical cell, the ionic liquid was fully saturated and the pressure in the headspace reached a constant value after sealing the cell and the electrochemical corrosion of the copper electrode was started after 5 minutes. A voltage of 3.5 V was applied across the cell, with copper as the positive electrode and a constant current of 11.5 mA was rapidly achieved and maintained throughout the experiment.

Figure 8:
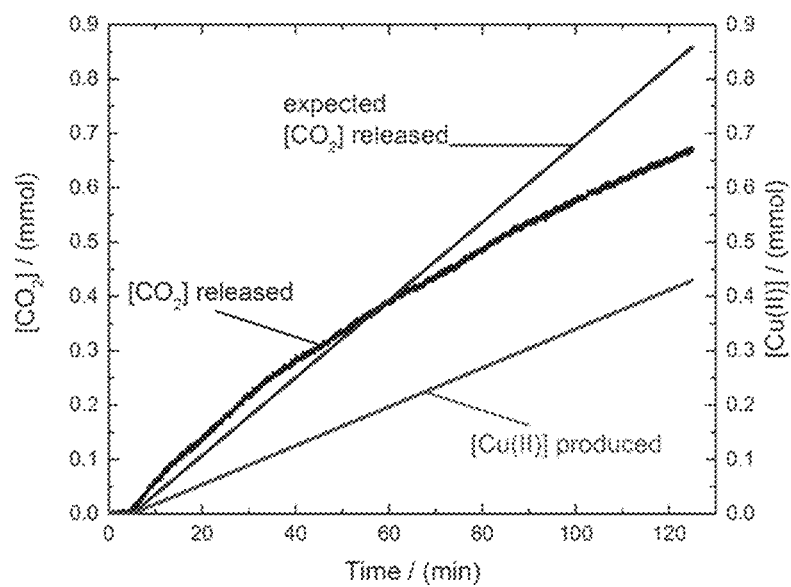
FIG. 8 shows a plot of the expected and experimentally determined number of moles of $CO_2$ released in the headspace of the electrochemical cell, and the number of moles of Cu(II) produced.

The pressure in the headspace increased due to the release of $CO_2$ and this change in pressure was used to calculate the number of moles of $CO_2$ released, shown in FIG. 8. As shown in FIG. 1, for every Cu(II) generated, two molecules of $CO_2$ are released. The number of moles of Cu(II) produced is shown in FIG. 8, this was calculated from the total charge passed through the electrolyte, while the expected number of moles of $CO_2$ to be released is shown by the blue line.

TGA results show that at the maximum uptake of $CO_2$ at 50° C. and 70° C. is 2.97 wt % and 0.97 wt % respectively. By interpolation, it can be assumed that at 65° C. the $CO_2$-saturated RTIL contained ~1.5 wt % $CO_2$. This amounts to 0.495 g (12.4 mmol) of $CO_2$. The curve of the moles of $CO_2$ released, shown in FIG. 8, shows an initial release of $CO_2$ slightly larger than expected, which could be due to the release of some of the physiorbed $CO_2$ along with the chemisorbed $CO_2$. However, the curve shows a constantly declining rate of release and after two hours, only about 10% of the captured $CO_2$, as predicted by TGA results, is released. Also, the number of moles of $CO_2$ released after 60 minutes are less than expected given the number of moles of Cu(II) ions produced by the oxidation of the copper electrode, calculated from the total charge in the experiment. This is due to the recapture of some of the released $CO_2$ by the newly regenerated ionic liquid molecules which lose their chelated Cu(II) ion to reduction at the platinum counter electrode. As the system reaches equilibrium, there will be a constant flux of Cu(II) ions between the copper electrode, where they are generated, and the platinum counter electrode, where they are electroplated and subsequently removed from the ionic liquid electrolyte freeing two ionic liquid molecules to recapture the newly released $CO_2$. This will result in plateauing of the headspace pressure, i.e. the moles of $CO_2$ released, as the rates of release and recapture balance. Figure S9 shows the deposited (electroplated) copper on the platinum electrode after the two hour-long experiment. Furthermore, as the pressure of $CO_2$ in the headspace increases, the vapor-liquid equilibrium (VLE) is shifted to favor the dissolution of more $CO_2$ into the electrolyte.

The problem of the declining rate of release is an artifact of the batch and sealed experimental setup in this work, in some embodiments, may be circumvented by separating the platinum counter electrode from the ionic liquid electrolyte in glass vial with a porous membrane which contains a solution of sacrificial reduction compound, such as benzoquinone, which can be reduced at the electrode in lieu of the Cu(II) ions that are generated due to the corrosion of the copper working electrode. In which case, the overall concentration of Cu(II) ions in the ionic liquid electrolyte increases with time at a constant rate that is proportional to the current passing through the cell and thus most of the captured $CO_2$ can be released, also at a constant rate (ignoring reabsorption). However, this is not expected to manifest in the continuous and open system since the flow in their reported system involves a constant Cu(II) ion concentration in the release chamber half-cell, as the generated ions are constantly advected away from the corroding electrode in the anode half-cell, where $CO_2$ is released, to the reducing (electroplating) electrode in the cathode half cell, where EDA is regenerated.

Example 5

In a non-limiting example, Values for the viscosity of the ionic liquid, [HButylen][Tf$_2$N], were measured at different temperatures. Viscosity is a parameter that affects the mass transport of both $CO_2$ and Cu ions. The magnitude of the activation energy ($E_a$) is an indication of the difficulty of transfer of molecules through the liquid matrix.

A rheometer, fitted with a cone and plate (2°/40 mm), was used to determine viscosities between 40 and 100° C. First, viscosity was measured as a function of shear stress (10-1000 Pa) at 40° C. to ensure the materials gave linear responses with no shear history. Measurements were then repeated at 50, 60, 70, 80, 90, 100° C. Once Newtonian behavior was verified, the viscosities were recorded as a function of temperature under constant shear stress. The resulting values of viscosity for a given temperature are shown in Table 1 below:

TABLE 1

| Temperature (° C.) | Viscosity (Pa s) |
|---|---|
| 40 | 0.182 |
| 50 | 0.100 |
| 60 | 0.065 |
| 70 | 0.043 |
| 80 | 0.030 |
| 90 | 0.021 |
| 100 | 0.016 |

Like most ionic liquids [HButylen][Tf$_2$N] exhibited Newtonian behavior in the range studied. It has a viscosity at 40° C. at around 182 cP. Surprisingly, however, the viscosity falls off rapidly with temperature and at 100° C. is only 16 cP (similar to that of ethylene glycol).

In order to calculate the activation energies for viscous flow from the Arrhenius Equation (Equation 6), semi-logarithmic Arrhenius-like plots were made. In Equation 6, η represents viscosity, R is the universal gas constant and T is the temperature.

$$\eta = \eta_\infty \exp{\frac{E_a}{RT}} \qquad (6)$$

The activation energy for viscous flow has been calculated to be Ea=39 kJ mol$^{-1}$.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed:

1. A method for capturing a Lewis acid gas, comprising:
providing a system comprising a first zone and a second zone in fluid connection with the first zone, wherein:
the first zone comprises a functional ionic liquid comprising a cation and an anion; and
the second zone comprises a complexation agent capable of associating and/or disassociating the cation to and/or from the functional ionic liquid upon exposure to an electrical potential;
exposing the ionic liquid to the Lewis acid gas in the first zone, wherein the cation associates with the Lewis acid gas to form a cation-Lewis-acid-gas complex; and
exposing the cation-Lewis-acid-gas complex to the complexation agent in the second zone,
wherein the step of exposing the cation-Lewis-acid-gas complex to the complexation agent in the second zone comprises applying an electrical potential to the complexation agent, and
wherein the complexation agent associates with the cation to form a cation-complexation agent complex and the Lewis acid gas is released to form free Lewis acid gas.

2. The method according to claim 1, wherein the cation is represented by the following structural formula:

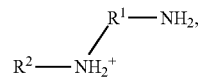

wherein:
R$^1$ has the formula: $(C(R)_2)_n$, in which R is H or an optionally substituted $C_1$-$C_3$ alkyl group; and n is 1, 2, 3, 4, 5, or 6; and $R^2$ has the formula: $(C(R')_2)_m$—R", in which R' is H or an optionally substituted $C_1$-$C_3$ alkyl group; R" is H or an optionally substituted $C_1$-$C_3$ alkyl group; and m is 1, 2, 3, 4, 5, 6, 7, 8, 9, or 10.

3. The method according to claim 2, wherein n is 2.

4. The method according to claim 3, wherein R is H.

5. The method according to claim 2, wherein m is 6 and R" is H.

6. The method according to claim 2, wherein $R^2$ is 2-ethylhexyl.

7. The method according to claim 1, wherein the anion of the functional ionic liquid is selected from the group consisting of boron tetrafluoride, phosphorus tetrafluoride, phosphorus hexafluoride, alkylsulfonate, fluoroalkylsulfonate, arylsulfonate, bis(alkylsulfonyl)amide, bis(fluoroalkylsulfonyl)amide, bis(arylsulfonyl)amide, (fluoroalkylsulfonyl)(fluoroalkylcarbonyl)amide, halide, nitrate, nitrite, sulfate, hydrogensulfate, alkyl sulfate, aryl sulfate, carbonate, bicarbonate, carboxylate, phosphate, hydrogen phosphate, dihydrogen phosphate, hypochlorite, and an anionic site of a cation-exchange resin.

8. The method according to claim 1, wherein the anion of the functional ionic liquid is selected from the group consisting of boron tetrafluoride, phosphorus hexafluoride, methanesulfonate, trifluoromethanesulfonate, benzenesulfonate, p-toluenesulfonate, bis(methanesulfonyl)amide, bis(trifluoromethanesulfonyl)amide, bis(benzenesulfonyl)amide, or bis(p-toluenesulfonyl)amide.

9. The method according to claim 1, wherein the anion of the functional ionic liquid is selected from the group consisting of methanesulfonate, trifluoromethanesulfonate, benzenesulfonate, p-toluenesulfonate, bis(methanesulfonyl)amide, bis(trifluoromethanesulfonyl)amide, bis(benzenesulfonyl)amide, or bis(p-toluenesulfonyl)amide.

10. The method according to claim 1, wherein the anion of the functional ionic liquid is selected from the group consisting of bis(methanesulfonyl)amide, bis(trifluoromethanesulfonyl)amide, bis(benzenesulfonyl)amide, or bis(p-toluenesulfonyl)amide.

11. The method according to claim 1, wherein the anion of the functional ionic liquid is bis(trifluoroethanesulfonyl)amide.

12. The method according to claim 1, wherein the cation of the functional ionic liquid is dicationic or polycationic.

13. The method according to claim 1, wherein the anion of the functional ionic liquid is dianionic or polyanionic.

14. The method according to claim 1, wherein the Lewis acid gas is $CO_2$ and the cation-Lewis-acid-gas complex is a cation-$CO_2$ complex.

15. The method according to claim 14, wherein the step of exposing the ionic liquid to $CO_2$ in the first zone comprises scrubbing a flue gas.

16. The method according to claim 1, wherein the step of applying the electrical potential to the complexation agent comprises oxidizing an anode of an electrochemical cell.

17. The method according to claim 1, wherein the first zone comprises a flue gas scrubbing zone.

18. The method according to claim 1, wherein the second zone comprises an anode compartment of an electrochemical cell.

19. The method according to claim 1, further comprising disassociating the complexation agent from the cation-complexation agent complex to restore the cation.

20. The method according to claim 1, wherein the complexation agent comprises copper.

* * * * *